United States Patent [19]
Meer

[11] Patent Number: 5,190,053
[45] Date of Patent: Mar. 2, 1993

[54] METHOD AND APPARATUS FOR ELECTRICAL SUBLINGUAL STIMULATION

[75] Inventor: Jeffrey A. Meer, 7380 St. Auburn Dr., Birmingham, Mich. 48010

[73] Assignee: Jeffrey A. Meer, revocable living trust, West Bloomfield, Mich.

[21] Appl. No.: 662,565

[22] Filed: Feb. 28, 1991

[51] Int. Cl.$^5$ .............................................. A61N 1/05
[52] U.S. Cl. .................................. 128/787; 128/716; 128/725; 128/419 G
[58] Field of Search ............... 128/642, 784, 802, 787, 128/419 G, 716, 725

[56] References Cited

U.S. PATENT DOCUMENTS

| | | | |
|---|---|---|---|
| 3,277,892 | 10/1966 | Tepper | 128/787 X |
| 4,334,542 | 6/1982 | Takinishi et al. | 128/642 |
| 4,519,400 | 5/1985 | Brenman et al. | 128/787 X |
| 4,830,008 | 5/1989 | Meer | 128/721 X |

FOREIGN PATENT DOCUMENTS

| | | | |
|---|---|---|---|
| 1424792 | 9/1988 | U.S.S.R. | 128/642 |
| 1553140 | 3/1990 | U.S.S.R. | 128/787 |

*Primary Examiner*—Lee S. Cohen
*Assistant Examiner*—Brian L. Casler
*Attorney, Agent, or Firm*—Brooks & Kushman

[57] ABSTRACT

An intra-oral, sublingual electrode device for the electrical stimulation of a genioglossus muscle to maintain the patency of an upper airway in the treatment of sleep apnea syndrome is disclosed as having a plurality of electrodes mounted to a support that is securable within an oral cavity to maintain optimally effective electrode disposition. The support is temporarily and conveniently securable, for example, to a patient's lower teeth. The support includes a plurality of electrode support members, each supporting and electrically insulating an electrode. Electrical conductors connected to the electrodes are routed through portions of the device to enhance the latter's stability, to protect the conductors and to position the conductors for comfortable egress from the patient's mouth. Various apparatus for fastening the assembly in place and for urging the electrodes into comfortable and effective contact are also disclosed, as are various methods of electrical muscle stimulation.

20 Claims, 4 Drawing Sheets

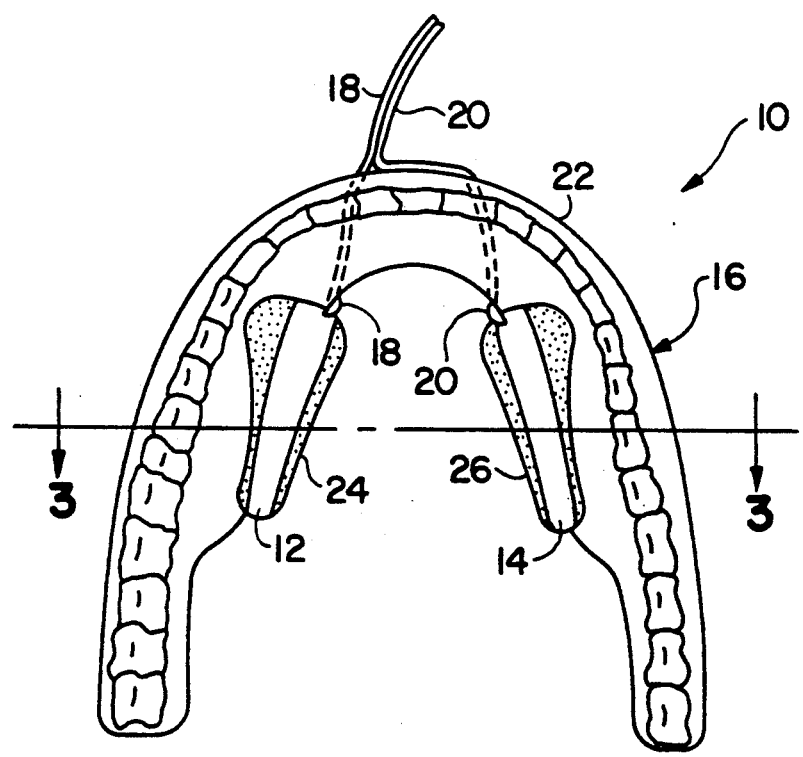
FIG. 1
FIG. 2
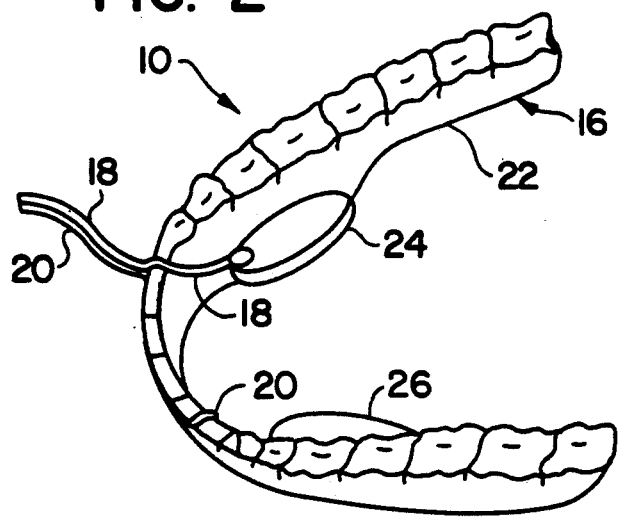

METHOD AND APPARATUS FOR ELECTRICAL SUBLINGUAL STIMULATION

TECHNICAL FIELD

This invention relates to the application of sublingual electrical stimulation to the genioglossus muscle for the treatment of sleep apnea syndrome.

BACKGROUND ART

Sleep apnea syndrome, a medical condition characterized by the periodic cessation of breathing during sleep, has been classically defined as embracing two types. Central sleep apnea syndrome involves a repeated loss of respiratory effort during sleep, and obstructive sleep apnea syndrome involves a repeated number of apneic episodes during sleep caused by an obstruction of the upper airway.

Treatment for central sleep apnea syndrome has included the use of various medications, such as protriptyline, medroxyprogesterone, acetazolamide, theophylline and nicotine, and the avoidance of central nervous system depressants such as sedatives and alcohol. Such treatment has occasionally been of some benefit but has rarely been completely effective.

Electrical stimulation has also been used to regulate and control the diaphragm of a patient. This procedure, called diaphragmatic pacing, is disclosed in *Direct Diaphragm Stimulation*, by J. Mugica et el., PACE, Vol. 10, January–February, 1987, Part II; *Preliminary Test of a Muscular Diaphragm Pacing System on Human Patients*, by J. Mugica et al., from *Neurostimulation: An Overview*, 1983, pages 263–279: and *Electrical Activation of Respiration*, by Nochomovitez, IEEE Eng. in Medicine and Biology, June 1983. Many patients suffering from central sleep apnea syndrome also have some degree of obstructive sleep apnea syndrome, however; and this condition worsens when inspiratory force is augmented by a pacer. Additionally, ventilation induced by activation of the diaphragm tends to collapse the upper airway of the patient upon inspiration and to draw the patient's tongue anteriorly downward, obstructing the patient's throat.

Treatment for obstructive sleep apnea syndrome has included a surgical procedure to correct severe retrognathia and other surgical procedures such as uvulopalatopharyngoplasties and tonsillectomies. Such procedures have met with some success but have often been unacceptable to patients.

Weight reduction and the use during sleeping hours of various devices, such as airways and tongue and jaw positioners, have been partially effective; but these measures are inconvenient, cumbersome and uncomfortable, which makes their continued use for long periods unlikely.

The only completely effective procedure for treating obstructive sleep apnea is tracheostomy, but considerable morbidity and aesthetically based rejection attends such a procedure.

It has been demonstrated that upper airway muscles that maintain patency lose tone during obstructive apneic episodes. A description of this may be found in *The Human Tongue During Sleep: Electromyographic Activity of the Genioglossus Muscle*, by Sauerland and Harper, Experimental Neurology, 1976, 51, 160–170.

It has also been demonstrated that submental electrical stimulation can reverse upper airway obstruction, presumably by contracting the genioglossus muscle, which produces an anterior displacement of the base of the tongue. A description of this may be found in *Effects of Submental Electrical Stimulation During Sleep on Upper Airway Patency in Patients with Obstructive Sleep Apnea*, by Miki et al., Am Review of Resp Diseases, 1989, 140, 1285–1289. Other studies have suggested that submental electrical stimulation is not effective in many patients because electrical current must be passed through skin, subcutaneous tissue and genioglossus muscle. The amount of current required causes pain in many patients. It is possible to more effectively stimulate the genioglossus muscle by using electrodes implanted subcutaneously, but this procedure exposes patients to the risk of infection, pain and complications such as hypoglossal nerve and genioglossus muscle damage. There are also risks associated with general anesthesia.

While each of the procedures described functions with a certain degree of efficiency, none disclose the advantages provided by the electrical sublingual stimulation device of the present invention as is hereinafter more fully described.

DISCLOSURE OF INVENTION

An object of the present invention is to provide an effective, convenient and comfortable device and method for electrically stimulating genioglossus muscles using noninvasive electrodes.

In realizing the aforementioned and other objects, the method for electrically stimulating a genioglossus muscle to maintain upper airway patency in the treatment of sleep apnea syndrome includes providing a plurality of electrodes; providing a plurality of electrical conductors, each conductor being electrically connected to a different one of the electrodes to conduct electrical pulses to the electrode to which each conductor is connected; providing a support for supporting the electrodes to maintain an optimally effective intra-oral disposition of the electrodes, a first electrode being maintained in contact with the mucosa of the floor of, and on one side of the frenulum of, a patient's mouth and a second electrode being maintained in contact with the mucosa on the other side of the frenulum; providing an electrical pulse source connected to the conductors, the source, which may be a pulse generator, having an output providing pulses of selectable mode, polarity, amplitude, current, pulse width and frequency, positioning the support means within a mouth so that the electrodes are effectively and comfortably in contact with the mucosa; and supplying electrical pulses from the source thereof to the electrodes such that the pulses pass from at least one electrode on one side of the frenulum, through the genioglossus muscle, to at least one electrode on the other side of the frenulum.

In one configuration of the invention, the inspiratory efforts of a patient are monitored; and the mode, polarity, amplitude, current, width, frequency and time of application of the electrical pulses are controlled as a function of the monitored efforts. The contractions of the patient's inspiratory muscles are compared with a threshold contraction; and, if the comparison indicates respiratory distress, an electrical signal is generated and applied at an appropriate time to stimulate muscles that move the patient's tongue anteriorly to maintain upper airway patency.

In another configuration of the invention, a patient's intrathoracic pressure is monitored; and the pressure is compared with a threshold pressure. If the comparison indicates respiratory distress, an electrical signal is generated and applied at an appropriate time to stimulate muscles that move the patient's tongue anteriorly to maintain upper airway patency.

Additional details of the monitoring methods may be found in U.S. Pat. No. 4,830,008, issued on May 16, 1989 to Jeffrey A. Meer, the inventor of the present invention, the patent being titled *Method and System for Treatment of Apnea*, the contents of the patent being incorporated herein by reference.

A sublingual electrode device for the electrical stimulation of a genioglossus muscle to maintain upper airway patency in the treatment of sleep apnea syndrome includes a plurality of electrodes and a plurality of electrical conductors. Each conductor is electrically connected to a different one of the electrodes to conduct electrical pulses from a source thereof to the electrode to which each conductor is connected. A support is provided for supporting the electrodes to maintain an optimally effective intra-oral disposition of the electrodes. A first electrode is maintained in contact with the mucosa of the floor of, and on one side of the frenulum of, a patient's mouth; and a second electrode is maintained in contact with the mucosa on the other side of the frenulum so that electrical pulses will pass through a portion of the genioglossus muscle.

An intra-oral, sublingual electrode system for the electrical stimulation of a genioglossus muscle includes a plurality of electrodes and a plurality of electrical conductors. Each conductor is electrically connected to a different one of the electrodes to conduct electrical pulses to the electrode to which each conductor is connected. A support is provided for supporting the electrodes to maintain an optimally effective intra-oral disposition of the electrodes. A first electrode is maintained in contact with the mucosa of the floor of, and on one side of the frenulum of, a patient's mouth; and a second electrode is maintained in contact with the mucosa on the other side of the frenulum. An electrical pulse source is connected to the conductors, &he source having an output providing electrical pulses having selectable properties of mode, polarity, amplitude, current, pulse width, and frequency.

The objects, features and advantages of the present invention are readily apparent from the following detailed description of the best mode for carrying out the invention when taken in connection with accompanying drawings.

BRIEF DESCRIPTION OF DRAWINGS

In the drawings, in which like reference characters indicate corresponding parts in all the views:

FIG. 1 is an inverted plan view of a first embodiment of a sublingual electrode device;

FIG. 2 is a perspective view of the device shown by FIG. 1;

Figure 9:
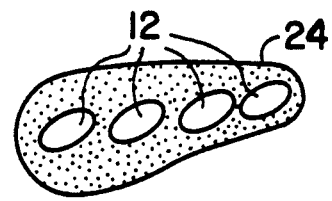
Figure 11:
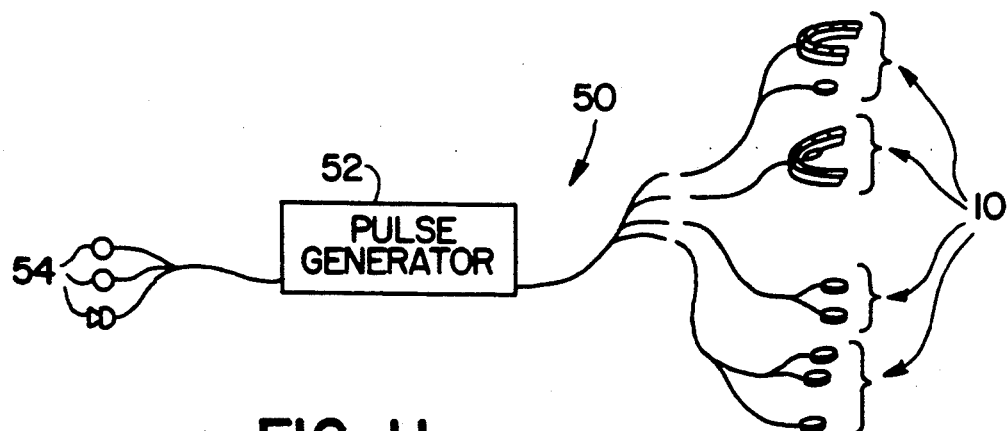
Figure 10:
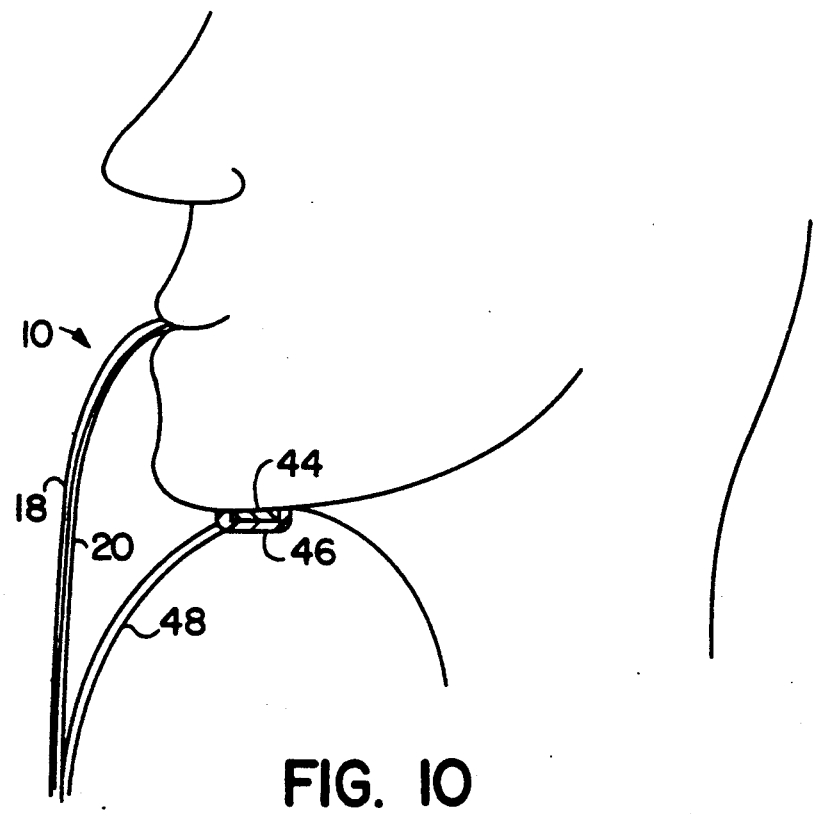

FIG's. 7 and 8 are each a sectional view of alternate elements of the sublingual electrode device;

FIG. 9 is an inverted plan view of an alternate element of the sublingual electrode device;

FIG. 10 is a side view showing a portion of a patient's head and illustrating the positioning of a fifth embodiment of the sublingual electrode device; and FIG. 11 is a partially schematic view of a sublingual electrode system showing several alternate embodiments of elements thereof.

BEST MODE FOR CARRYING OUT THE INVENTION

With reference to FIG's. 1 and 2 of the drawings, a first embodiment of a sublingual electrode device for the electrical stimulation of a genioglossus muscle to maintain upper airway patency in the treatment of sleep apnea syndrome is generally indicated by reference numeral 10. The device 10 includes a first electrode 12 and a second electrode 14. The first electrode 12 and the second electrode 14 are supported by support means, or a support, generally indicated by reference numeral 16. The device also includes a first electrical conductor 18 and a second electrical conductor 20. The first conductor 18 is electrically connected to the first electrode 12, and the second conductor 20 is electrically connected to the second electrode 14.

Figure 3:
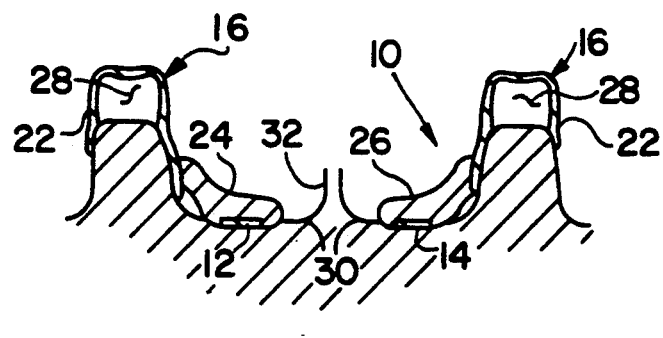
FIG. 3 is a sectional view taken along the line 3—3 of the device of FIG. 1 and shown fitted on the mandible of a patient.

In the first embodiment shown, the support 16 includes a support structure 22, a first support member 24 and a second support member 26. The support structure 22 is formed of a plastic material, which may be acetate or any material having similar properties, and, as shown by FIG. 3 of the drawings, is molded to fi&. over the teeth 28 of a patient's mandible. The fit of the support structure 22 over the teeth 28 is such that the device 10 is comfortable maintained in the position shown but may be easily removed by the patient.

The first support member 24 is mounted to the support structure 22 such that it presses the first electrode 12 mounted thereon against the sublingual mucosa 30 on the floor of the patient's mouth on the right side of the patient's frenulum 32. The second support member 26 is mounted to the support structure 22 such that it presses the second electrode 14 mounted thereon against the sublingual mucosa 30 on the floor of the patient's mouth on the left side of the patient's frenulum 32.

The support structure 22 may be formed by first making, in a manner commonly used by dentists, a plaster model of a patient's lower mandibular teeth and the floor of his or her mouth. A plastic sheet, such as one made of clear acetate, is then heated and vacuum-molded over the model to form a "tray" that conforms to the shape of the teeth and portions of associated gums. Such trays are commonly used for fabricating mouth guards used in the treatment of bruxism.

The support members 24 and 26 may be formed, using the portion of the plaster model conforming to the floor of the patient's mouth, of a material such as polyvinyl siloxane ("Imprint" Dental Impression Material made by 3-M Company, Minneapolis, MN), which is nontoxic and biocompatible with mouth tissues. The electrodes 12 and 14 may be formed of silver foil strips or a material having similar properties. The silver foil could be relatively thin, for example, having a typical thickness on the order of 0.001 inch. If the foil is mounted to the support members 24 and 26 with adhesive, silicon cement such as Silastic Cement (made by 3-M Company) may be used. The conductors are preferably made from fine, flexible, Teflon-coated wire. The wires are preferably soldered to the silver foils with solder comprising ninety-six percent tin and four percent silver and may be routed within portions of the support structure to enhance the latter's stability, to protect the conductors and to position the conductors for comfortable egress from the mouth.

Figure 4:
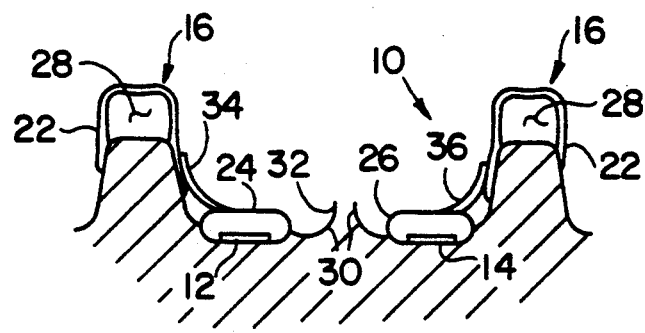
FIG. 4 is a view, similar to that of FIG. 3, of a second embodiment of the sublingual electrode device shown thereby.

Shown by FIG. 4 of the drawings is a second embodiment of the sublingual electrode device 10 wherein the first and second support members, 24 and 26 respectively, are mounted to the support structure 22 with, and resiliently biased against the mucosa 30 by, first and second spring members 34 and 36 respectively. It should be understood that the first and second spring members, 34 and 36 respectively, may be leaf-type springs as shown or any type of resilient biasing means familiar to anyone skilled in the art.

Figure 5:
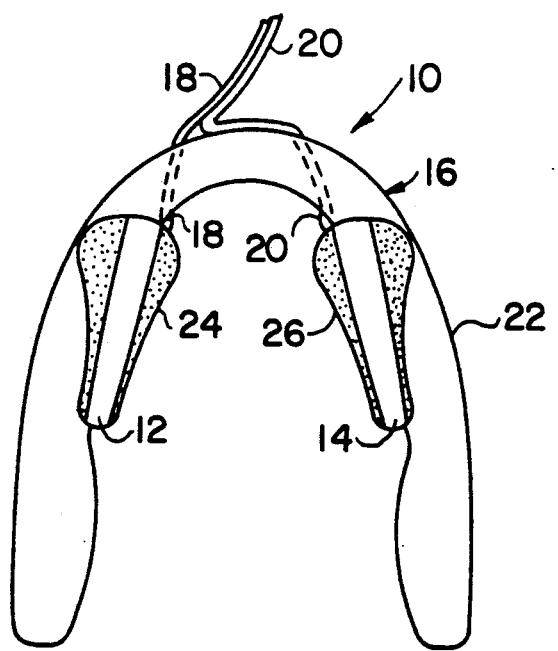
FIG. 5 is an inverted plan view, similar to that of FIG. 1, of a third embodiment of the sublingual electrode device shown thereby.

It should also be understood that the support structure 22 may be fashioned in a number of configurations, in addition to that shown, to maintain the first and second electrodes 12 and 14 effectively and comfortably in contact with the mucosa 30. For example, shown by FIG. 5 of the drawings is a third embodiment of the sublingual electrode device 10 wherein the support structure 22 has a configuration conforming at least partially to the shape of a portion of the underside of a patient's tongue so that the tongue can comfortably maintain the support structure in position to ensure effective contact between the electrodes and the associated mucosa of the floor of the patient's mouth. Other configurations (not shown) may include a support structure having resilient clips or elastic bands to secure the support structure to the patient's teeth.

Figure 6:
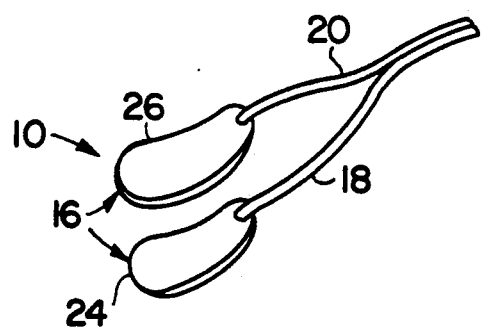
FIG. 6 is a perspective view of a fourth embodiment of the sublingual electrode device.

A fourth embodiment of the sublingual electrode device 10 is shown by FIG. 6 of the drawings. In this embodiment, the support 16 and the first and second electrodes, 12 and 14 respectively, are unitary bodies formed of an electrically conductive gel-adhesive material that maintains contact between the electrodes and associated mucosa of the floor of a patient's mouth and also conducts electrical pulses to the mucosa from first and second conductors, 18 and 20 respectively, electrically connected to the electrodes 12 and 14 respectively. The conductive gel-adhesive may be that used for "H-Wave" Electrical Dental Anesthesia Units (manufactured by H-Wave, Inc. of California).

Figure 7:
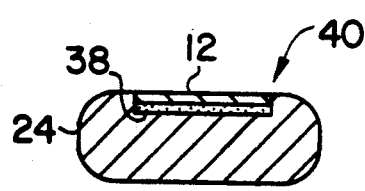
Figure 8:
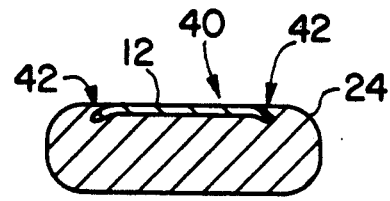

As illustrated by FIG. 7, an electrode 12 may be mounted to a support member 24 with an adhesive 38. The support member 24 may have a recess, generally indicated by reference numeral 40, within which to receive the electrode 12 so that no rough or sharp edges are created that might irritate contacted mucosa. FIG. 8 of the drawings shows a support member 24 having a recess, generally indicated by reference numeral 40, to receive an electrode 12, the recess having peripheral margins, generally indicated by reference numeral 42, overlapping borders of the electrode 12 disposed therein to retain the electrode 12 within the recess 40.

Another type of support member 24 is illustrated by FIG. 9 of the drawings. This type has a plurality of electrodes 12 mounted to or within the support member 24 to provide a like number of exposed surfaces to contact associated mucosa. These electrodes may be electrically connected together (not shown) within the body of the support member 24 so that only one conductor need be routed therefrom.

With reference to FIG. 10 of the drawings, shown is a fifth embodiment of the sublingual electrode device 10. This embodiment includes a third electrode 44 mounted to a third support member 46. As shown, the third electrode 44 is designed to provide submental contact, that is, contact with the skin beneath a patient's chin. Contact may be maintained by a number of well known means; for example, the third electrode 44 and the third support member 46 may be held in position by an adhesive. A third electrical conductor 48 is electrically connected to the third electrode 44. The third electrode 44 would be used in combination with the first and second electrodes, 12 and 14 respectively, pulse current flowing from the former to the latter and/or vice versa.

An intra-oral, sublingual electrode system 50 is illustrated by FIG. 11. The system 50 includes a sublingual electrode device 10 and sensors 54 connected to an electrical pulse source, or pulse generator, 52. The sensors 54 are attached to a patient to monitor inspiratory-associated conditions, and one of the devices 10 is fitted within the patient's mouth to impart electrical pulses, generated by the pulse generator 52 in response to the conditions sensed by the sensors 54, to the patient's sublingual mucosa to increase the tone of the genioglossus muscle or to stimulate the muscle to a point where the patient's tongue is moved anteriorly to maintain upper airway patency.

The pulse generator 52 has an output that provides electrical pulses having selectable properties of mode, polarity, amplitude, current, pulse width, and frequency. The pulse mode may be direct current or alternating current; and, if the pulses are direct current, their polarity may be negative or positive. The polarity of the electrical pulses is periodically reversed according to predetermined criteria so that electrical current flows through the genioglossus muscle in both directions to ensure a balanced stimulation of both sides of the genioglossus muscle.

A commercially available pulse generator 52 that provides pulses having many of the previously mentioned variables is a Medtronic Respond II Neuromuscular Stimulator (made by Medtronic, Inc., Minneapolis, MN). The stimulator may be set to provide, with a twenty-percent duty factor, direct current pulses having an amplitude of 18 volts, a frequency of 50 Hertz and a duration of 500 microseconds.

In one configuration of the invention, the inspiratory efforts of a patient are monitored; and the mode, polarity, amplitude, current, width, frequency and time of application of the electrical pulses are controlled as a function of the monitored efforts. The contractions of the patient's inspiratory muscles are compared with a threshold contraction; and, if the comparison indicates respiratory distress, an electrical signal is generated and applied at an appropriate time to stimulate muscles that move the patient's tongue anteriorly to maintain upper airway patency.

In another configuration of the invention, a patient's intrathoracic pressure is monitored; and the pressure is compared with a threshold pressure. If the comparison indicates respiratory distress, an electrical signal is generated and applied at an appropriate time to stimulate muscles that move the patient's tongue anteriorly to maintain upper airway patency.

Yet another method for detecting the onset of apnea uses a microphone placed over a patient's trachea. A Model TR-21 microphone, manufactured by Grass Instrument Company, Quincy, MA, may be used for this purpose.

In one application of the invention, no stimulating pulses are applied if normal upper airway activity is sensed. In another application, stimulating pulses are applied during the early portion of a patient's every inspiration.

OPERATION OF THE SYSTEM

The sublingual electrode system 50, shown by FIG. 11, used in the treatment of sleep apnea syndrome electrically stimulates a patient's genioglossus muscle to maintain upper airway patency. Before the patient retires, the electrode device 10 is fitted in his or her mouth, as shown by FIG. 3, so that a first electrode 12 is maintained in contact with the mucosa 30 of the floor of the patient's mouth on one side of the frenulum 32 thereof, and a second electrode 14 is maintained in contact with the mucosa 30 on the other side of the frenulum 32. When properly positioned, the support structure 22 fits over and is held in place by the patient's lower mandibular teeth 28.

If stimulation of the patient's tongue is to be responsive to inspiratory-associated conditions, the sensors 54 are positioned at appropriate locations on the patient's body. In one embodiment of the invention, the inspiratory efforts of the patient are monitored; and, in another embodiment, the patient's intrathoracic pressure is monitored. The sensed conditions are compared to threshold values; and, if the comparison indicates respiratory distress, an electrical signal is generated and applied at an appropriate time to stimulate muscles that move the patient's tongue anteriorly to maintain upper airway patency.

While the best mode for carrying out the invention has been described in detail, those familiar with the art to which this invention relates will recognize various alternative designs and embodiments for practicing the invention as defined by the following claims.

What is claimed is:

1. A sublingual electrode device for applying stimulating electrical pulses from a source thereof to a patient's genioglossus muscle to maintain upper airway patency int eh treatment of sleep apnea syndrome, the device comprising:
    a plurality of electrodes;
    a plurality of electrical conductors, each conductor being electrically connected to a different one of the electrodes to conduct electrical pulses form the source thereof to the electrode to which each conductor is connected; and
    support means for sublingually supporting the electrodes to maintain an optimally effective intra-oral, sublingual disposition of the electrodes.

2. The device defined by claim 1, wherein the support means and the plurality of electrodes comprise a plurality of unitary bodies formed of an electrically conductive gel-adhesive material that maintains contact between the electrodes and associated mucosa and also conducts electrical pulses from the conductors to the mucosa.

3. The device defined by claim 2, further including an electrical pulse source connected to the conductors, the source having an output providing electrical pulses having selectable properties of mode, polarity, amplitude, current, pulse width, and frequency, and wherein the selectable properties are a function of monitored inspiratory efforts of a patient.

4. The device defined by claim 3, further including a third electrode to contact skin beneath a patient's chin, the third electrode being used in combination with the first and second electrodes, pulse current flowing between the first and second electrodes and the third electrode.

5. The device defined by claim 3, wherein the electrical pulses are direct current and the selectable properties of the electrical pulses further include polarity.

6. The device defined by claim 3, wherein the electrical pulses are alternating current.

7. The device defined by claim 1, wherein the support means comprises:
    a support structure; and
    a plurality of support members mounted to the support structure, at least one of the plurality of electrodes being mounted to each support member, a first electrode being maintained in contact with the mucosa of the floor of, and on one side of the frenulum of, the patient's mouth and a second electrode being maintained in contact with the mucosa on the other side of the frenulum.

8. The device defined by claim 7, further comprising resilient biasing means for resiliently biasing the support members away from the support structure to ensure effective and comfortable contact between the electrodes and associated mucosa of the floor of the patient's mouth.

9. The device defined by claim 7, wherein each electrode is formed of an elongate strip of conductive material.

10. The device defined by claim 7, further including an adhesive to secure each electrode to an associated support member.

11. The device defined by claim 7, wherein each support member includes a recess to receive an electrode, each recess having peripheral margins overlapping borders of the electrode disposed therein to retain the electrode within the recess.

12. The device defined by claim 7, wherein the support structure has a configuration conforming at least partially to the shape of a portion of the underside of a patient's tongue so that the tongue can comfortably maintain the support structure in position to ensure effective contact between the electrodes and associated mucosa of the floor of the patient's mouth.

13. The device defined by claim 7, wherein a portion of the support structure has a configuration conforming at least partially to lower teeth in the patient's mouth for attachment thereto, to maintain the support structure in position to ensure effective sublingual contact between the electrodes and associated mucosa of the floor of the patient's mouth.

14. The device defined by claim 7, wherein at least one of the electrical conductors connected to an electrode disposed on one side of the frenulum and at least one of the electrical conductors connected to an electrode disposed on the other side of the frenulum are routed through portions of the support means to enhance the stability of the support means, to protect the conductors and to position the conductors for comfortable egress from the patient's mouth.

15. The device defined by claim 7, further including a third electrode to contact skin beneath a patient's chin, the third electrode being used in combination with the first and second electrodes, pulse current flowing between the first and second electrodes and the third electrode.

16. A method for electrically stimulating a patient's genioglossus muscle to maintain upper airway patency int he treatment of sleep apnea syndrome, the method comprising the steps of:
provniding a plurality of electrodes;
providing a plurality of electrical conductors, each conductor being electrically connected to a different one of the electrodes, to conduct electrical pulses to the electrode to which each conductor is connected;
providing support means for sublingually supporting the electrodes to maintain an optimally effective intra-oral, sublingual disposition of the electrodes, a first electrode being maintained in contact with the mucosa of the floor of, and on one side of the frenulum of, the patient's mouth and a second electrode being maintained in contact with the mucosa on the other side of the frenulum;
providing an electrical pulse source connected to the conductors, the source having an output providing electrical pulses of selectable mode, polarity, amplitude, current, pulse width and frequency;
positioning the support means within the patient's mouth so that the electrodes are effectively and comfortably in contact with the mucosa; and
supplying, at predetermined times, electrical pulses from form the source thereof to the electrodes such that the pulses pass from at least one electrode on one side of the frenulum, through the genioglossus muscle, to at least one electrode on the other side of the frenulum.

17. The method as defined by claim 16, further comprising a step of width, frequency and time of application of the electrical pulses prior to the step of supplying the electrical pulses.

18. The method as defined by claim 16, further comprising the steps of
monitoring the inspiratory efforts of a patient; and
selecting the mode, polarity, amplitude, current, width, frequency and time of application of the electrical pulses as a function of the monitored inspiratory efforts prior to the step of supplying the pulses.

19. The method as defined by claim 17, further comprising the step of periodically reversing the polarity of the electrical pulses according to predetermined criteria to ensure a balanced stimulation of both sides of the genioglossus muscle.

20. The method as defined by claim 18, further comprising the step of periodically reversing the polarity of the electrical pulses according to predetermined criteria.

* * * * *

UNITED STATES PATENT AND TRADEMARK OFFICE
CERTIFICATE OF CORRECTION

PATENT NO. : 5,190,053

DATED : March 2, 1993

INVENTOR(S) : JEFFREY A. MEER

It is certified that error appears in the above-identified patent and that said Letters Patent is hereby corrected as shown below:

Col. 3, line 10, after "of" insert -- Sleep --.

Col. 3, line 41, after "conductors," delete "&he" and insert -- the --.

Col. 4, line 33, after "to" delete "fi&" and insert -- fit --.

Claim 1, col. 7, line 44, after "patency" delete "int eh" and insert -- in the --.

Claim 16, col. 9, line 27, after "from" delete "form".

Claim 17, col. 10, line 6, after "of" insert -- selecting the mode, polarity, amplitude, current, --.

Signed and Sealed this

Fourth Day of January, 1994

Attest:

BRUCE LEHMAN

*Attesting Officer*     Commissioner of Patents and Trademarks